(12) United States Patent
Kumar et al.

(10) Patent No.: US 9,415,109 B2
(45) Date of Patent: Aug. 16, 2016

(54) STABLE NON-AGGREGATING NUCLEIC ACID LIPID PARTICLE FORMULATIONS

(71) Applicant: ALNYLAM PHARMACEUTICALS, INC., Cambridge, MA (US)

(72) Inventors: Varun Kumar, Cambridge, MA (US); Akin Akinc, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/412,957

(22) PCT Filed: Jul. 3, 2013

(86) PCT No.: PCT/US2013/049207
§ 371 (c)(1),
(2) Date: Jan. 5, 2015

(87) PCT Pub. No.: WO2014/008334
PCT Pub. Date: Jan. 9, 2014

(65) Prior Publication Data
US 2015/0165039 A1    Jun. 18, 2015

Related U.S. Application Data

(60) Provisional application No. 61/668,566, filed on Jul. 6, 2012.

(51) Int. Cl.
| | | |
|---|---|---|
| *A61K 47/26* | (2006.01) | |
| *A61K 9/127* | (2006.01) | |
| *A61K 47/48* | (2006.01) | |
| *A61K 9/51* | (2006.01) | |
| *A61K 47/10* | (2006.01) | |
| *A61K 47/18* | (2006.01) | |
| *A61K 48/00* | (2006.01) | |
| *C12N 15/113* | (2010.01) | |
| *C12N 15/88* | (2006.01) | |

(52) U.S. Cl.
CPC ............... *A61K 47/26* (2013.01); *A61K 9/1272* (2013.01); *A61K 9/5123* (2013.01); *A61K 47/10* (2013.01); *A61K 47/18* (2013.01); *A61K 47/48815* (2013.01); *C12N 15/113* (2013.01); *A61K 48/00* (2013.01); *C12N 15/1137* (2013.01); *C12N 15/88* (2013.01); *C12N 2310/14* (2013.01); *C12Y 304/21021* (2013.01)

(58) Field of Classification Search
CPC .............................. A61K 31/713; A61K 47/26
See application file for complete search history.

(56) References Cited

FOREIGN PATENT DOCUMENTS

| WO | WO-2008078102 A2 | 7/2008 |
| WO | WO-2010144740 A1 | 12/2010 |

OTHER PUBLICATIONS

Barichello, et al., "Agitation During Lipoplex Formation Harmonizes the Interaction of SiRNA to Cationic Liposomes", International Journal of Pharmaceutics, 2012, 430:359-365.

Mozafari, "Nanoliposomes: Preparation and Analysis", Chapter 2, "Liposomes, Methods in Molecular Biology", 2010, 605:29-50.

Zhao, et al., "Comparative Study of the In Vitro and In Vivo Characteristics of Cationic and Neutral Liposomes", International Journal of Nanomedicine, 2011, 6:3087-3098.

International Search Report issued in PCT/US2013/049207 on Sep. 18, 2013.

*Primary Examiner* — Jon E Angell
(74) *Attorney, Agent, or Firm* — Blank Rome LLP

(57) ABSTRACT

The present invention relates to stable lipid nanoparticle pharmaceutical formulations which are substantially free of large aggregates (e.g., aggregates greater than 1 μm in size) and include a substantially non-ionic medium.

29 Claims, 4 Drawing Sheets

STABLE NON-AGGREGATING NUCLEIC ACID LIPID PARTICLE FORMULATIONS

This application is the U.S. national phase of International Application No. PCT/US2013/049207, filed Jul. 3, 2013, which claims the benefit of U.S. Provisional Application No. 61/668,566, filed Jul. 6, 2012, the entire contents of which are hereby incorporated by reference.

FIELD OF THE INVENTION

The present invention relates to stable lipid nanoparticle pharmaceutical formulations which are substantially free of large aggregates (e.g., aggregates greater than 1 μm in size) and include a substantially non-ionic medium.

BACKGROUND OF THE INVENTION

The development of short interfering RNA sequences (siRNAs) as therapeutics has been hindered by problems in delivering the siRNA to its target. siRNA rapidly undergoes enzymatic degradation resulting in a short half-life in the blood, and has poor cellular update and tissue bioavailability. As a result, there has been significant research on delivering siRNA in lipid nanoparticles (LNPs).

Many LNPs include components to minimize aggregation. The inclusion of pegylated lipids into LNPs is known to inhibit aggregation, however, PEG can affect the intracellular delivery and trafficking of non-viral vectors. See, e.g., Heyes et al., *J. Control. Release,* 112 (2006) 280-290. The instructions for some pharmaceuticals indicate that the formulation should be shaken before use in order to break up aggregates and minimize their effect during dosing. However, shaking may not sufficiently break-up aggregates, and there is a risk that the medical practitioner will not perform this function.

There is, therefore, a need for improved stable LNP formulations with minimal aggregation.

SUMMARY OF THE INVENTION

The present inventors have discovered that aggregation of lipid nanoparticles (LNPs), especially those for delivering nucleic acids, can be inhibited with a formulation that is substantially free of negative counter-ions (i.e., anions). The medium for the formulation preferably is non-ionic or de-ionized, such as de-ionized water. The formulation can tolerate some anions as discussed below.

In one aspect, the present invention relates to a pharmaceutical formulation suitable for parenteral administration comprising (a) lipid nanoparticles in (b) a medium. Each nanoparticle comprises a cationic lipid and an active pharmaceutical ingredient (such as a nucleic acid). The formulation has one or more of the following characteristics:
  (i) the medium is substantially free of anions,
  (ii) the medium is non-ionic or substantially non-ionic, and
  (iii) the formulation has a pH less than the pKa of the cationic lipid.

In one preferred embodiment, the formulation has a pH ranging from about 4 to about 6.

In addition or as an alternative to the three characteristics above, the formulation is sufficiently stable such that, when the formulation is subjected to vortexing for 60, 90, or 120 seconds the particle size distribution of the lipid nanoparticles does not substantially change. For instance, the $d_{50}$ of the lipid nanoparticles after vortexing is not more than 40 or 50% greater than that of the lipid nanoparticles before vortexing. In one particular embodiment, when the lipid nanoparticles have a unimodal particle size distribution before vortexing, the lipid nanoparticles also exhibit a unimodal particle size distribution after vortexing.

In certain embodiments, the lipid nanoparticles in the formulation have a $d_{98}$ of less than 1 micron, such as less than about 500 nm, less than about 400 nm, less than about 300 nm, less than about 250 nm, less than about 200 nm, less than about 150 nm or less than about 100 nm. For example, the lipid nanoparticles have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. For instance, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

According to another aspect, the present invention relates to a pharmaceutical formulation suitable for parenteral administration comprising lipid nanoparticles in a medium, where each lipid nanoparticle comprises a cationic lipid and an active pharmaceutical ingredient (such as a nucleic acid), and the lipid nanoparticles have a $d_{98}$ of less than 1 micron, such as less than about 500 nm, less than about 400 nm, less than about 300 nm, less than about 250 nm, less than about 200 nm, less than about 150 nm or less than about 100 nm. For instance, the lipid nanoparticles may have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. In one embodiment, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

In one preferred embodiment, the $d_{50}$, $d_{98}$ or $d_{99}$ of the lipid nanoparticles in the formulation does not vary by more than 40, 30, 20, 10, or 5% after 1 month of storage at 4° C. In one embodiment, after 1 month of storage at 4° C., the lipid nanoparticles in the formulation have $d_{50}$, $d_{98}$ and/or $d_{99}$ values as set forth above. For instance, after 1 month storage at 4° C., the lipid nanoparticles in the formulation have $d_{98}$ or $d_{99}$ of less than 1 micron, such as less than about 500 nm, less than about 400 nm, less than about 300 nm, less than about 250 nm, less than about 200 nm, less than about 150 nm or less than about 100 nm.

In yet another embodiment, the lipid nanoparticles in the formulation of the present invention have a single mode particle size distribution (i.e., they are not bi- or poly-modal).

The formulation preferably has a low ionic strength, for example, an ionic strength less than about 50 mM, about 40 mM, about 30 mM, about 20 mM, about 15 mM, about 10 mM, about 5 mM, about 2 mM, or about 1 mM. (The ionic strength of the formulation can be measured using techniques known to the skilled person, for example using a conductivity meter.)

The medium may comprise a non-ionic or substantially non-ionic diluent, and preferably includes a non-ionic or substantially non-ionic diluent that does not destabilize the formulation. In one embodiment, the non-ionic or substantially non-ionic diluent increases the stability of the lipid nanoparticles, such as against mechanical disturbances, and/or inhibits the aggregation of the lipid nanoparticles. The medium may comprise water. In a preferred embodiment, the medium is deionized (e.g., deionized water). The water in the medium may have been purified by reverse osmosis. In a preferred embodiment, the medium contains less than about 50 ppm of mineral acid(s), such as less than about 40 ppm, less than about 30 ppm, less than about 20 ppm, less than about 10 ppm, less than about 5 ppm or less than about 1 ppm of mineral acid(s).

In one embodiment, the formulation further comprises an acid, wherein the molar concentration ratio of (a) the concentration of the anions formed from the acid to (b) the concentration of the acid is less than about 0.5, such as less than about 0.4, less than about 0.3, less than about 0.2 or less than about 0.1. In a particular embodiment, the molar ratio of anion concentration to acid concentration is less than about 0.2 to about 0.5. The anions present in the formulation may be derived from the acid in the medium. In one embodiment, the anion is a monovalent anion (such as an anion derived from acetic acid).

In another embodiment, the medium is free or substantially free of buffer. In one embodiment, the medium contains less than 2, 1, 0.5, 0.2, 0.1, or 0.05% by weight of buffer (based upon 100% total weight of the medium).

In yet another embodiment, the medium is free or substantially free of all or one or more of citrate, saline, L-histidine HCl, histidine, phosphate, and imidazole HCl. In one embodiment, the medium contains less than 2, 1, 0.5, 0.2, 0.1, or 0.05% by weight of each these components or of these components in total (based upon 100% total weight of the medium)

In one preferred embodiment, the lipid nanoparticles comprise:
  (a) a nucleic acid,
  (b) a cationic lipid,
  (c) a non-cationic lipid (such as a neutral lipid),
  (d) an aggregation reducing agent (such as polyethylene glycol (PEG) or PEG-modified lipid), and
  (e) optionally, a sterol.

In one embodiment, the cationic lipid has a pKa ranging from about 4 to about 11, and preferably from about 5 to about 7.

Because the formulations of the present invention exhibit reduced aggregation, they may include a decreased amount of the aggregation reducing agent (such as PEG or PEG-modified lipid) than prior lipid nanoparticles. In one embodiment, the formulation includes less than about 3, about 2, about 1.5, about 1, or about 0.5 mole percent of the aggregation reducing agent (such as PEG or PEG-modified lipid), based upon the total moles of lipid (e.g., total moles of cationic lipid, non-cationic lipid, sterol, and aggregation reducing agent) in the lipid nanoparticle.

In one embodiment, the formulation further comprises one or more isotonicity agents. Preferably, the formulation includes a sufficient amount of the isotonicity agent(s) to render the formulation physiologically isotonic (i.e., have a pharmaceutically acceptable osmolality) in order to avoid cell distortion or lysis.

In a preferred embodiment, the active pharmaceutical ingredient in the lipid nanoparticles is a nucleic acid, such as a siRNA. The nucleic acid-lipid particle preferably has an encapsulation efficiency of greater than about 90, 92, 95, or 98%, after storage of the formulation for 1 month at about 4° C.

The formulations described herein may be solutions or suspensions.

According to another aspect, the present invention relates to a method for decreasing, inhibiting, or preventing the aggregation of lipid nanoparticles in a pharmaceutical formulation for parenteral administration. The particles comprise a cationic lipid and an active pharmaceutical ingredient such as a nucleic acid. The method includes dispersing the lipid nanoparticles in a medium, where the formulation has one or more of the following characteristics:
  (i) the medium is substantially free of anions,
  (ii) the medium is non-ionic or substantially non-ionic, and
  (iii) the formulation has a pH less than the pKa of the cationic lipid.

Yet another embodiment is a method of preparing a pharmaceutical formulation of the present invention comprising:
  (i) preparing lipid nanoparticles comprising a cationic lipid and an active pharmaceutical ingredient (such as a nucleic acid) in a first medium comprising a buffer; and
  (ii) changing the first medium to a second medium which is (a) non-ionic or substantially non-ionic and/or (b) free of or substantially free of anions.

In one preferred embodiment, the second medium comprises deionized water, such as that prepared by reverse osmosis.

In one preferred embodiment, the formulation has a pH ranging from about 4 to about 6, such as a pH ranging from about 4 to about 5 or a pH ranging from about 5 to about 6.

The method may further include the step of adding an isotonicity agent, such as those described herein.

DETAILED DESCRIPTION OF THE INVENTION

Definitions

Figure 1:
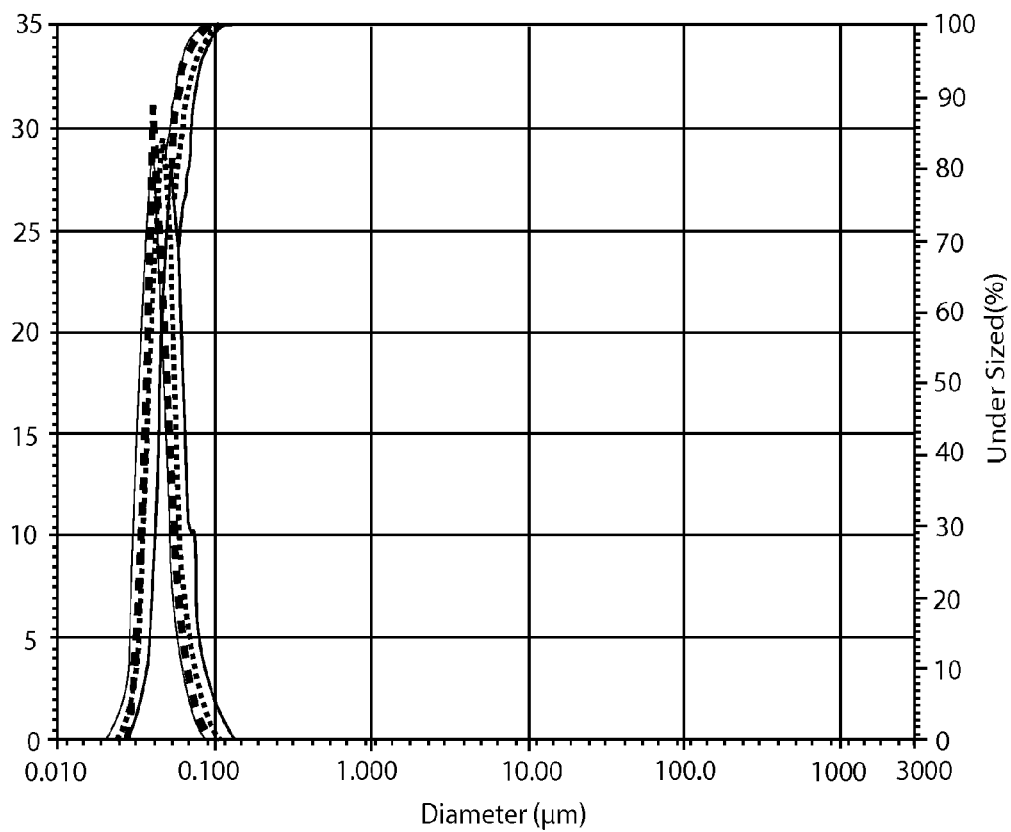
FIG. 1 shows the particle size distribution of a lipid nanoparticle formulation prepared (Formulation 2) as described in Example 1 with deionized water after preparation and after being vortexed for 30, 60, or 120 seconds.

The term "subject" or "patient" refers to a mammal, such as a human, domestic animal, such as a feline or canine subject, farm animal (e.g., bovine, equine, caprine, ovine, and porcine subject), wild animal (whether in the wild or in a zoological garden), research animal, such as mouse, rat, rabbit, goat, sheep, pig, dog, and cat, avian species, such as chicken, turkey, and songbird. The "subject" or "patient" can also be a plant.

The terms "treat" and "treatment" refer to (a) relief from or alleviation of at least one symptom of a disorder in a subject, (b) relieving or alleviating the intensity and/or duration of a manifestation of a disorder experienced by a subject, (c) slowing or reversing the progression of such condition, and (d) arresting, delaying the onset (i.e., the period prior to clinical manifestation of a disorder) and/or reducing the risk of developing or worsening a disorder.

As used herein, the term "intravenous infusion" or "IV infusion" refers to a method of administration of a composition directly into the vein of a patient. IV infusion allows for direct administration of a pharmaceutical formulation to the bloodstream of a patient. This can be performed, for example, via subcutaneous or intradermal infusion. IV infusion can be performed in many ways, including through the use of an injection needle, or with an infusion pump. It can be provided as, for example, a continuous infusion, an intermittent infusion, a patient-controlled infusion, or a circadian infusion.

An "isotonicity agent" generally refers to a compound that is physiologically tolerated and imparts a suitable tonicity to a formulation to prevent the net flow of water across cell membranes that are in contact with the formulation.

The term "encapsulation efficiency" as used herein refers to the percentage of nucleic acid in the lipid nanoparticles that is not degraded after exposure to serum or a nuclease assay that would significantly degrade free nucleic acids. Encapsulation efficiency can be measured as follows:

Dilute the lipid nanoparticle formulation to ~5 μg/mL in 1×TE buffer. Place 50 μL of the sample in a well in a polystyrene 96 well plate, and 50 μL in the well below it. Add 50 μL of 1×TE buffer to the top well, and 50 μL of 2% Triton X-100 to the bottom well. For the reference wells, replace the sample with 50 μL of 1×TE buffer.

Allow the 96 well plate to incubate at 35° C. for 15 minutes. During this time, remove the Quant-iT™ RiboGreen® from the −20° C. storage and allow it to thaw. Once thawed, dilute the RiboGreen 1:100 in 1×TE buffer. After the 15 minute incubation, add 100 μL of diluted RiboGreen reagent to each well, mixing thoroughly by pipetting up and down. Try to avoid creating bubbles while mixing; the samples containing Triton X-100 are especially prone to bubble formation.

Once addition of the RiboGreen is complete, the plate is then read by a fluorescence plate reader (FITC settings); after subtracting the fluorescence values of the blanks from each sample well, the percent of free siRNA may be determined by dividing the fluorescence of the intact liposome sample (no Triton X-100) by the fluorescence value of the disrupted liposome sample (with Triton X-100).

Entrapped fraction=1−free fraction

Encapsulation efficiency=100*Entrapped fraction

The term "fully encapsulated" as used herein indicates that the nucleic acid in the particles is not significantly degraded after exposure to serum or a nuclease assay that would significantly degrade free nucleic acids. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

Active Pharmaceutical Ingredients

The active pharmaceutical ingredient can be any compound suitable for incorporation into a lipid nanoparticle. In one embodiment, the active pharmaceutical ingredient is encapsulated within an aqueous interior of the lipid nanoparticle. In another embodiment, the active pharmaceutical ingredient is present within one or more lipid layers of the lipid nanoparticle. In yet another embodiment, the active pharmaceutical ingredient is bound to the exterior or interior of the lipid surface of the lipid nanoparticle.

The active pharmaceutical ingredient can be any compound capable of exerting a desired effect on a cell, tissue, organ, or subject. Such effects may be biological, physiological, or cosmetic, for example. The active pharmaceutical ingredient can be a nucleic acid, peptide, polypeptide (e.g., an antibody), cytokine, growth factor, apoptotic factor, differentiation-inducing factor, cell surface receptor or a corresponding ligand, or hormone. Suitable active pharmaceutical ingredient include, but are not limited to, anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs (e.g., anti-arrhythmic agents), vasoconstrictors, hormones, steroids, and oncology drugs (e.g., an anti-tumor agent, an anti-cancer drug, or anti-neoplastic agent).

In a preferred embodiment, the active pharmaceutical ingredient is a nucleic acid. The nucleic acid can be an interfering RNA (such as a siRNA), an antisense oligonucleotide, a DNAi oligonucleotide, a ribozyme, an aptamer, a plasmid, or any combination of any of the foregoing. For example, the nucleic acid can be encoded with a product of interest including, but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, and vaccines or mixtures thereof. In one embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long (e.g., 17-21 or 19-21 nucleotides long). In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. The term "microRNA mimic" refers to synthetic non-coding RNAs (i.e. the miRNA is not obtained by purification from a source of the endogenous miRNA) that are capable of entering the RNAi pathway and regulating gene expression.

The nucleic acid that is present in a lipid nanoparticle can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The nucleic acid can be conjugated to one or more ligands.

In further embodiments, the nucleic acid is selected from an interfering RNA, an antisense oligonucleotide, a DNAi oligonucleotide, a ribozyme, an aptamer, a plasmid, and any combination of any of the foregoing. In one embodiment, the RNA is selected from siRNA, aiRNA, miRNA, Dicer-substrate dsRNA, shRNA, ssRNAi oligonucleotides, and any combination of any of the foregoing.

In a more preferred embodiment, the active pharmaceutical ingredient is an siRNA (e.g., an siRNA having a duplex region that is 17-21 or 19-21 nucleotides long). Formulations containing siRNA are useful in down-regulating the protein levels and/or mRNA levels of target proteins. The siRNA may be unmodified oligonucleotides or modified, and may be conjugated with lipophilic moieties such as cholesterol.

In another embodiment, the active pharmaceutical ingredient is a micro RNA.

In one preferred embodiment, the active pharmaceutical ingredient (e.g., a nucleic acid) is fully encapsulated in the lipid nanoparticle.

Cationic Lipids

The lipid nanoparticle may include any cationic lipid suitable for forming a lipid nanoparticle. Preferably, the cationic lipid carries a net positive charge at about physiological pH.

The cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid at physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethyl ammonium propane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28,31-tetraen-19-yl 4-(dimethylamino)butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination of any of the foregoing.

Other cationic lipids include, but are not limited to, N,N-distearyl-N,N-dimethylammonium bromide (DDAB), 3β-(N—(N',N'-dimethylaminoethane)-carbamoyl)cholesterol (DC-Chol), N-(1-(2,3-dioleyloxyl)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010.

Other suitable amino lipids include those having alternative fatty acid groups and other dialkylamino groups, including those in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain embodiments, the protonatable lipids have a pKa of the protonatable group in the range of about 4 to about 11, e.g., a pKa of about 5 to about 7.

Lipid particles can include two or more cationic lipids. The cationic lipids can be selected to contribute different advantageous properties. For example, cationic lipids that differ in properties such as amine $pK_a$, chemical stability, half-life in circulation, half-life in tissue, net accumulation in tissue, or toxicity can be used in the lipid nanoparticle. In particular, the cationic lipids can be chosen so that the properties of the mixed-lipid particle are more desirable than the properties of a single-lipid particle of individual lipids.

Net tissue accumulation and long term toxicity (if any) from the cationic lipids can be modulated in a favorable way by choosing mixtures of cationic lipids instead of selecting a single cationic lipid in a given formulation. Such mixtures can also provide better encapsulation and/or release of the active pharmaceutical ingredient.

In one example, a series of structurally similar compounds can have varying $pK_a$ values that span a range, e.g. of less than 1 $pK_a$ unit, from 1 to 2 $pK_a$ units, or a range of more than 2 $pK_a$ units. Within the series, it may be found that a $pK_a$ in the middle of the range is associated with an enhancement of advantageous properties (greater effectiveness) or a decrease in disadvantageous properties (e.g., reduced toxicity), compared to compounds having $pK_a$ values toward the ends of the range. In such a case, two (or more) different compounds having $pK_a$ values toward opposing ends of the range can be selected for use together in a lipid nanoparticle. In this way, the net properties of the lipid nanoparticle (for instance, charge as a function of local pH) can be closer to that of a particle including a single lipid from the middle of the range. Cationic lipids that are structurally dissimilar (for example, not part of the series of structurally similar compounds mentioned above) can also be used in a mixed-lipid nanoparticle.

In some cases, two or more different cationic lipids may have widely differing $pK_a$ values, e.g., differing by 3 or more $pK_a$ units. In this case, the net behavior of a mixed lipid nanoparticle will not necessarily mimic that of a single-lipid particle having an intermediate $pK_a$. Rather, the net behavior may be that of a particle having two distinct protonatable (or deprotonatable, as the case may be) site with different $pK_a$ values. In the case of a single lipid, the fraction of protonatable sites that are in fact protonated varies sharply as the pH moves from below the $pK_a$ to above the $pK_a$ (when the pH is equal to the $pK_a$ value, 50% of the sites are protonated). When two or more different cationic lipids may have widely differing $pK_a$ values (e.g., differing by 3 or more $pK_a$ units) are combined in a lipid nanoparticle, the lipid nanoparticle can show a more gradual transition from non-protonated to protonated as the pH is varied.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle).

In one embodiment, the ratio of cationic lipid to nucleic acid is from about 3 to about 15, such as from about 5 to about 13 or from about 7 to about 11.

Non-Cationic Lipids

The non-cationic lipid can be a neutral lipid, an anionic lipid, or an amphipathic lipid. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., lipid particle size and stability of the lipid particle in the bloodstream. Preferably, the neutral lipid is a lipid having two acyl groups (e.g., diacylphosphatidylcholine and diacylphosphatidylethanolamine). In one embodiment, the neutral lipids contain saturated fatty acids with carbon chain lengths in the range of $C_{10}$ to $C_{20}$. In another embodiment, neutral lipids with mono or diunsaturated fatty acids with carbon chain lengths in the range of $C_{10}$ to $C_{20}$ are used. Additionally, neutral lipids having mixtures of saturated and unsaturated fatty acid chains can be used.

Suitable neutral lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (DMPC), distearoyl-phosphatidyl-ethanolamine (DSPE), SM, 16-O-monomethyl PE, 16-O-dimethyl PE, 18-1-trans PE, 1-stearoyl-2-oleoyl-phosphatidylethanolamine (SOPE), cholesterol, or a mixture thereof.

Anionic lipids suitable for use in lipid particles of the invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphipathic lipids refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used.

The non-cationic lipid can be from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the particle. In one embodiment, the lipid nanoparticles include from about 0% to about 15 or 45% on a molar basis of neutral lipid, e.g., from about 3 to about 12% or from about 5 to about 10%. For instance, the lipid nanoparticles may include about 15%, about 10%, about 7.5%, or about 7.1% of neutral lipid on a molar basis (based upon 100% total moles of lipid in the lipid nanoparticle).

Sterols

A preferred sterol is cholesterol.

The sterol can be about 10 to about 60 mol % or about 25 to about 40 mol % of the lipid particle. In one embodiment, the sterol is about 10, 15, 20, 25, 30, 35, 40, 45, 50, 55, or about 60 mol % of the total lipid present in the lipid particle. In another embodiment, the lipid nanoparticles include from about 5% to about 50% on a molar basis of the sterol, e.g., about 15 to about 45%, about 20 to about 40%, about 48%, about 40%, about 38.5%, about 35%, about 34.4%, about 31.5% or about 31% on a molar basis (based upon 100% total moles of lipid in the lipid nanoparticle).

Aggregation Reducing Agent

The aggregation reducing agent can be a lipid capable of reducing aggregation. Examples of such lipids include, but are not limited to, polyethylene glycol (PEG)-modified lipids, monosialoganglioside Gm1, and polyamide oligomers (PAO) such as those described in U.S. Pat. No. 6,320,017, which is incorporated by reference in its entirety. Other compounds with uncharged, hydrophilic, steric-barrier moieties, which prevent aggregation during formulation, like PEG, Gm1 or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613, each of which is incorporated by reference in its entirety.

The aggregation reducing agent may be, for example, a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-Cer14 or PEG-Cer20). The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). Other pegylated-lipids include, but are not limited to, polyethylene glycol-didimyristoyl glycerol (C14-PEG or PEG-C14, where PEG has an average molecular weight of 2000 Da) (PEG-DMG); (R)-2,3-bis(octadecyloxy)propyl-1-(methoxy poly(ethylene glycol)2000)propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl-1-(methoxy poly(ethylene glycol)2000)propylcarbamate)) (GalNAc-PEG-DSG); mPEG (mw2000)-diastearoylphosphatidyl-ethanolamine (PEG-DSPE); and polyethylene glycol-dipalmitoylglycerol (PEG-DPG). In one embodiment, the aggregation reducing agent is PEG-DMG. In another embodiment, the aggregation reducing agent is PEG-c-DMA.

The average molecular weight of the PEG moiety in the PEG-modified lipids can range from about 500 to about 8,000 Daltons (e.g., from about 1,000 to about 4,000 Daltons). In one preferred embodiment, the average molecular weight of the PEG moiety is about 2,000 Daltons.

The concentration of the aggregation reducing agent may range from about 0.1 to about 15 mol %, based upon the 100% total moles of lipid in the lipid particle. In one embodiment, the formulation includes less than about 3, 2, or 1 mole percent of PEG or PEG-modified lipid, based upon the total moles of lipid in the lipid particle.

In another embodiment, the lipid nanoparticles include from about 0.1% to about 20% on a molar basis of the PEG-modified lipid, e.g., about 0.5 to about 10%, about 0.5 to about 5%, about 10%, about 5%, about 3.5%, about 1.5%, about 0.5%, or about 0.3% on a molar basis (based on 100% total moles of lipids in the lipid nanoparticle).

Lipid Nanoparticles (LNPs)

The lipid nanoparticles may have the structure of a liposome. A liposome is a structure having lipid-containing membranes enclosing an aqueous interior. Liposomes may have one or more lipid membranes. Liposomes can be single-layered, referred to as unilamellar, or multi-layered, referred to as multilamellar. When complexed with nucleic acids, lipid particles may also be lipoplexes, which are composed of cationic lipid bilayers sandwiched between DNA layers.

The formulation is preferably substantially free of aggregates of lipid nanoparticles. For instance, the formulation may have a $d_{90}$ (i.e., 90% of the particles have a particle size) less than about 1, about 0.9, about 0.8, about 0.7, or about 0.6 µm. In one embodiment, the formulation includes less than about 5, about 4, about 3, about 2, or about 1% by volume of aggregates greater than about 2, about 1.5, about 1, or about 0.8 µm.

In certain embodiments, the lipid nanoparticles in the formulation have a $d_{98}$ of less than 1 micron, such as less than about 500 nm, less than about 400 nm, less than about 300 nm, less than about 250 nm, less than about 200 nm, less than about 150 nm or less than about 100 nm. For example, the lipid nanoparticles have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. For instance, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

In another embodiment, the lipid nanoparticles have a median diameter size of from about 50 nm to about 300 nm, such as from about 50 nm to about 250 nm, for example, from about 50 nm to about 200 nm.

In one preferred embodiment, the $d_{50}$, $d_{98}$ or $d_{99}$ of the lipid nanoparticles in the formulation does not vary by more than 40, 30, 20, 10, or 5% after 1, 3, 6, 9, 12, and 24 months of storage at 4° C. In one embodiment, after 1 month of storage at 4° C., the lipid nanoparticles in the formulation have $d_{50}$, $d_{98}$ and/or $d_{99}$ values as set forth above. For instance, after 1 month storage at 4° C., the lipid nanoparticles in the formulation have $d_{98}$ or $d_{99}$ of less than 1 micron, such as less than about 500 nm, less than about 400 nm, less than about 300 nm, less than about 250 nm, less than about 200 nm, less than about 150 nm or less than about 100 nm.

In yet another embodiment, the lipid nanoparticles in the formulation of the present invention have a single mode particle size distribution (i.e., they are not bi- or poly-modal).

The lipid nanoparticles may further comprise one or more lipids and/or other components in addition to those mentioned above. Other lipids may be included in the liposome compositions for a variety of purposes, such as to prevent lipid oxidation or to attach ligands onto the liposome surface. Any of a number of lipids may be present in lipid particles, including amphipathic, neutral, cationic, and anionic lipids. Such lipids can be used alone or in combination.

Additional components that may be present in a lipid particle include bilayer stabilizing components such as polyamide oligomers (see, e.g., U.S. Pat. No. 6,320,017, which is incorporated by reference in its entirety), peptides, proteins, and detergents.

Different lipid nanoparticles having varying molar ratios of cationic lipid, non-cationic (or neutral) lipid, sterol (e.g., cholesterol), and aggregation reducing agent (such as a PEG-modified lipid) on a molar basis (based upon the total moles of lipid in the lipid nanoparticles) are provided in Table 1 below.

TABLE 1

| Formulation No. | Molar Ratio of Lipids (Based upon 100% total moles of lipid in the lipid nanoparticle) | | | |
| --- | --- | --- | --- | --- |
| | Cationic Lipid | Non-Cationic (or Neutral) Lipid | Sterol | Aggregation Reducing Agent (e.g., PEG-lipid) |
| 1 | from about 35 to about 65% | from about 3 to about 12 or 15% | from about 15 to about 45% | from about 0.1 to about 10% (preferably from about 0.5 to about 2 or 3%) |

TABLE 1-continued

| Formulation No. | Cationic Lipid | Non-Cationic (or Neutral) Lipid | Sterol | Aggregation Reducing Agent (e.g., PEG-lipid) |
|---|---|---|---|---|
| 2 | from about 20 to about 70% | from about 5 to about 45% | from about 20 to about 55% | from about 0.1 to about 10% (preferably from about 0.5 to about 2 or 3%) |
| 3 | from about 45 to about 65% | from about 5 to about 10% | from about 25 to about 40% | from about 0.1 to about 3% |
| 4 | from about 20 to about 60% | from about 5 to about 25% | from about 25 to about 55% | from about 0.1 to about 5% (preferably from about 0.1 to about 3%) |
| 5 | about 40% | about 10% | about 40% | about 10% |
| 6 | about 35% | about 15% | about 40% | about 10% |
| 7 | about 52% | about 13% | about 30% | about 5% |
| 8 | about 50% | about 10% | about 38.5% | about 1.5% |

In one embodiment, the weight ratio of lipid to siRNA is at least about 0.5:1, at least about 1:1, at least about 2:1, at least about 3:1, at least about 4:1, at least about 5:1, at least about 6:1, at least about 7:1, at least about 11:1 or at least about 33:1. In one embodiment, the weight ratio of lipid to siRNA is from about 1:1 to about 35:1, about 3:1 to about 15:1, about 4:1 to about 15:1, or about 5:1 to about 13:1. In one embodiment, the weight ratio of lipid to siRNA is from about 0.5:1 to about 12:1.

In one embodiment, the lipid nanoparticles have an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

The Medium

The medium containing the lipid nanoparticles preferably is substantially free of negative counter-ions (i.e., anions). Without wishing to be bound by any particular theory, the inventors believe that the presence of negative counter-ions in an LNP formulation at least partially neutralizes the positively charged surface of the LNPs, thereby eliminating the aggregation reducing effect of charge repulsion.

The medium may comprise a non-ionic or substantially non-ionic diluent, and preferably includes a non-ionic or substantially non-ionic diluent that does not destabilize the formulation. In one embodiment, the non-ionic or substantially non-ionic diluent increases the stability of the lipid nanoparticles, such as against mechanical disturbances, and/or inhibits the aggregation of the lipid nanoparticles. The medium may comprise water. In a preferred embodiment, the medium is deionized (e.g., deionized water). The water in the medium may have been purified, for example, by reverse osmosis. In a preferred embodiment, the medium (such as water) contains less than about 50 ppm of mineral acid(s), such as less than about 40 ppm, less than about 30 ppm, less than about 20 ppm, less than about 10 ppm, less than about 5 ppm or less than about 1 ppm of mineral acid(s).

The medium may include an acid so long as it is not predominantly in its dissociated form. In one embodiment, the formulation further comprises an acid, wherein the ratio of (a) the concentration of the anions formed from the acid to (b) the concentration of the acid is less than about 0.5, such as less than about 0.4, less than about 0.3, less than about 0.2 or less than about 0.1. In a particular embodiment, the ratio of anion concentration to acid concentration is less than about 0.2 to 0.5. The anions present in the formulation may be derived from the acid in the medium. In one embodiment, the anion is a monovalent anion (such as an anion derived from acetic acid).

Isotonicity Agents

The isotonicity agent(s) included in the formulation are preferably substantially free of anions (e.g., substantially non-ionic), and more preferably are non-ionic. Suitable non-ionic isotonicity agents include, but are not limited to, polyols (e.g., a sugar alcohol such as a $C_3$-$C_6$ sugar alcohol), sugars (such as sucrose, fructose, dextrose, trehalose, or glucose), amino acids (such as glycine), and albumin. Suitable sugar alcohols include, but are not limited to, glycerol, erythritol, threitol, arabitol, xylitol, ribitol, sorbitol, mannitol, dulcitol and iditol. In one embodiment, the isotonicity agent is a sugar such as a glucose.

In one embodiment, the concentration of sugar (e.g., glucose) in the medium is at most about 300 mM, such as at most about 200, 100, 75, or 50 mM.

The amount of the isotonicity agent is preferably sufficient for the formulation to obtain an isotonic level.

In another embodiment, the formulation is free or substantially free of isotonicity agents.

Pharmaceutical Formulation

The concentration of lipid nanoparticles in the formulation may range from about 0.01 to about 50 mg/mL. In one embodiment, the concentration of lipid nanoparticles in the formulation ranges from about 0.1 to about 10 mg/mL, such as 0.5 to about 5 mg/mL. In another embodiment, the concentration of lipid nanoparticles in the formulation is about 0.5, about 0.75, about 1, about 1.5, about 2, about 2.5, about 3, about 4, or about 5 mg/mL.

The formulation may be administered parenterally, for example, intradermally, subcutaneously, intramuscularly, intravenously, or intraperitoneally. In one embodiment, the formulation is directly injected into a subject. In another embodiment, the formulation is added to an intravenous fluid which is intravenously administered. Because many intravenous fluids contain significant quantities of anions which may over time cause aggregation of LNPs, the formulation of the present invention is preferably added to the intravenous fluid shortly before (e.g., within 5, 10 or 15 minutes of) or simultaneously with the intravenous administration to the subject.

The formulation may further include additional pharmaceutically acceptable diluents, excipients, and/or carriers. Example of excipients include, but are not limited to, isotonicity agents, pH adjusting and buffering agents. The formulation may also include lipid-protective agents which protect lipids against free-radical and lipid-peroxidative damages on storage. Such agents include lipophilic free-radical quenchers, such as α-tocopherol and water-soluble iron-specific chelators, such as ferrioxamine.

The formulation can be sterilized by known sterilization techniques. The aqueous solutions can then be packaged for use or filtered under aseptic conditions and lyophilized, the lyophilized preparation being combined with a sterile aqueous solution prior to administration.

The concentration of lipid nanoparticles in the formulation can range, for example, from less than about 0.01% (e.g., at or at least about 0.05-5%) to as much as 10 to 30% by weight. The dose of lipid nanoparticles is dependent on many factors, including the disorder and active pharmaceutical ingredient. In one embodiment, the dose of lipid nanoparticles administered may range from about 0.01 and about 50 mg per kilogram of body weight (e.g., from about 0.1 and about 5 mg/kg of body weight).

The lipid formulation or lipid nanoparticles can be provided in kit form. The kit will typically be comprised of a container that is compartmentalized for holding the various elements of the kit. The kit may contain the lipid nanoparticles or the formulation, such as in dehydrated or concentrated form, with instructions for their rehydration or dilution and administration.

Methods of Manufacture

The lipid nanoparticles may be prepared by an in-line mixing method as follows. In this method, both the lipids (e.g., the cationic lipid, non-cationic lipid, sterol, and aggregation reducing agent) and the nucleic acid are added in parallel into a mixing chamber. The mixing chamber can be a simple T-connector. This method is disclosed, for example, in International Publication No. WO 2010/088537, U.S. Pat. No. 6,534,018 and U.S. Pat. No. 6,855,277, U.S. Patent Publication No. 2007/0042031 and *Pharmaceuticals Research*, Vol. 22, No. 3, March 2005, p. 362-372, which are hereby incorporated by reference in their entirety.

In one embodiment, individual and separate stock solutions are prepared—one containing lipid (e.g., the cationic lipid, non-cationic lipid, sterol, and aggregation reducing agent) and the other an active pharmaceutical ingredient, such as a nucleic acid (e.g., siRNA). A lipid stock solution containing a cationic lipid, non-cationic lipid, sterol, and an aggregation reducing agent (e.g., a PEG-modified lipid) is prepared by solubilizing the lipids in a solution of an alcohol (e.g., ethanol) at, for example, a lipid concentration of 25 mg/mL. The nucleic acid (e.g., siRNA) is solubilized in acetate buffer, for example, at a concentration of 0.8 mg/mL. For small scale, 5 mL of each stock solution may be prepared.

Preferably, the stock solutions are completely clear, and the lipids are completely solubilized before combining them with the nucleic acid. The stock solutions may be heated to completely solubilize the lipids.

The individual stock solutions (i.e., the lipid stock solution and the nucleic acid stock solution) may be combined by pumping each solution to a T-junction (i.e., by in-line mixing). This results in the formation of the lipid nanoparticles.

Following the formation of the lipid nanoparticles, the medium of the lipid nanoparticles may be exchanged to one which is (a) non-ionic or substantially non-ionic and/or (b) free of or substantially free of anions. This exchange can be performed by dialysis or tangential flow filtration.

For example, the lipid nanoparticles may be dialyzed into reverse osmosis/deionized (RO/DI) water, and then concentrated (e.g., using centrifuge tubes). The dispersion medium can then be changed to, for example, 300 mM glucose by adding an appropriate stock solution, for example, to give final lipid nanoparticles at ~1 mg/mL (based on siRNA).

Alternatively, the medium may be exchanged as follows. The lipid nanoparticles are diluted into RO/DI water. The diluted lipid nanoparticles are then concentrated using tangential flow filtration. The concentration step includes washing with 10× larger volume-compared to concentrated formulation volume-of RO/DI water. The dispersion medium can then be changed to, for example, 300 mM glucose by adding an appropriate stock solution, for example, to give final lipid nanoparticles at ~1 mg/mL (based on siRNA).

EXAMPLES

The examples below are provided to describe specific embodiments of the present invention. By providing these specific examples, the applicants do not limit the scope and spirit of the present invention.

Example 1

Lipid nanoparticles having the components shown in Table 2 below were prepared.

TABLE 2

| Component | Mole Percentage (Based on 100% of the lipid components in the LNP) |
|---|---|
| (6Z,9Z,28Z,31Z)-heptatriaconta-6,9,28,31-tetraen-19-yl-4-(dimethylamino) butanoate (MC3) | 50% |
| Distearoylphosphatidylcholine (DSPC) | 10% |
| Cholesterol | 38.5% |
| 1-(monomethoxy-polyethyleneglycol)-2,3-dimyristoylglycerol (PEG-DMG) | 1.5% |
| siRNA (AD-1596) | — |

MC3 can be prepared as described in International Publication No. WO 2010/144740, which is hereby incorporated by reference. The siRNA AD-1596 targets Factor VII and has the sequence shown below in Table 3.

TABLE 3

| Duplex # | Sense | Antisense |
|---|---|---|
| AD-1596 | GGAUCAUCUCAA GUCUUACdTdT | GUAAGACUUGAG AUGAUCCdTdT |

("G," "C," "A," "T" and "U" each refer to a ribonucleotide where the base is guanine, cytosine, adenine, thymidine and uracil, respectively. "dT" refers to a deoxyribonucleotide where the nucleobase is thymine, i.e., deoxyribothymine.)

The lipid nanoparticles was prepared as follows. MC3, DSPC, cholesterol, and PEG-DMG in the ratio recited in Table 2 were solubilized in ethanol at a total lipid concentration of 25 mg/mL.

A siRNA stock solution was prepared by solubilizing the siRNA AD-1596 in a low pH acetate buffer (pH=4) at 0.8 mg/mL. (The low pH acetate buffer, 25 mM acetate buffer (pH=4), was prepared using acetic acid (at 1.27 g/L) and sodium acetate (0.513 g/L) in reverse osmosis/deionized water.)

The stock solutions should be completely clear and the lipids should be completely solubilized before combining with the siRNA. Therefore, if it was determined appropriate, the stock solutions were heated to completely solubilize the lipids.

The individual stock solutions were combined by pumping each solution to a T-junction (i.e., by in-line mixing). Specifically, the ethanol solution (at 5 ml/min, via 0.01 in. PEEK tube) and aqueous buffer solution (at 15 mL/min, via 0.02 in. PEEK tube) were mixed through a T-junction (PEEK Tee body, IDEX).

Following mixing, the lipid nanoparticle solution was further treated according to one of the following two processes.

Process 1

The lipid nanoparticles were dialyzed into reverse osmosis/deionized (RO/DI) water, and then concentrated ~3× using 100 k centrifuge tubes (Ultracel 100 k centrifugal unit). The dispersion medium was then changed to either 1×PBS, or 300 mM glucose by adding appropriate stock to give a final lipid nanoparticles at ~1 mg/mL (based on siRNA).

Process 2

The lipid nanoparticles were diluted 5× into RO/DI water. The resultant diluted lipid nanoparticles were concentrated using tangential flow filtration. The concentration step includes washing with 10× larger volume—compared to concentrated formulation volume—of RO/DI water. The dispersion medium was then changed to either 1×PBS, or 300 mM glucose by adding appropriate stock to give final lipid nanoparticles at ~1 mg/mL (based on siRNA).

Example 2

The procedure in Example 1 except glucose was added to the final formulation to achieve a concentration of 300 mM glucose in the deionized water.

Comparative Example 1

The procedure in Example 1 was repeated using phosphate buffered saline (PBS) in lieu of deionized water.

Example 3

The particle size distribution of the lipid nanoparticles in the formulations prepared in Examples 1 and 2 and Comparative Example 1 (as prepared by Process 1) was measured using a Horiba Scientific LA-950 laser scattering particle size distribution analyzer (Horiba Ltd., Minami-Ku, Kyoto, Japan). All of the calculations were generated by the HORIBA laser diffraction software package. The results are displayed on a volume basis. A common approach for expressing laser diffraction results is to report the D10, D50, and D90 values based on a volume distribution.

The particle size distribution of the formulations prepared in Examples 1 and 2 was measured after their preparation and after being vortexed for 30, 60, or 120 seconds (Fisher_Scientific Mini Vortexer 00215365). The particle size distribution of the formulations prepared in Comparative Example 1 was measured after its preparation and after being vortexed for 3, 30, or 60 seconds.

Figure 2:
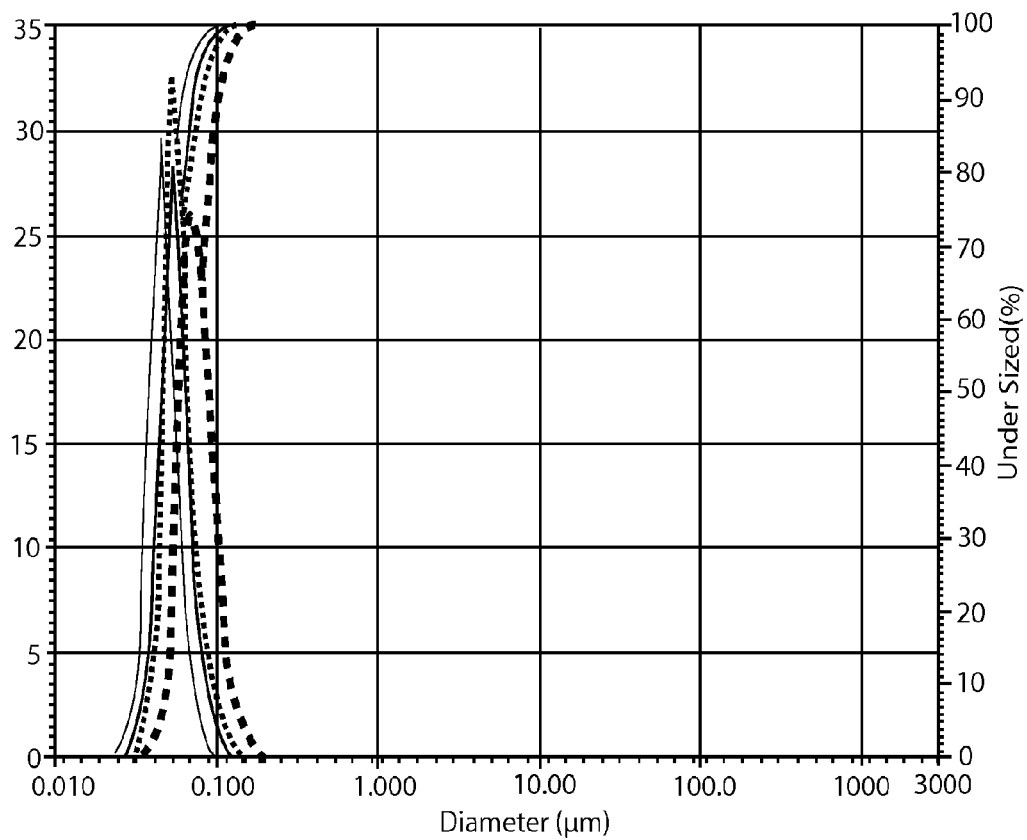
FIG. 2 shows the particle size distribution of a lipid nanoparticle formulation prepared (Formulation 3) as described in Example 2 with deionized water containing 300 mM glucose after preparation and after being vortexed for 30, 60, or 120 seconds.
Figure 3:
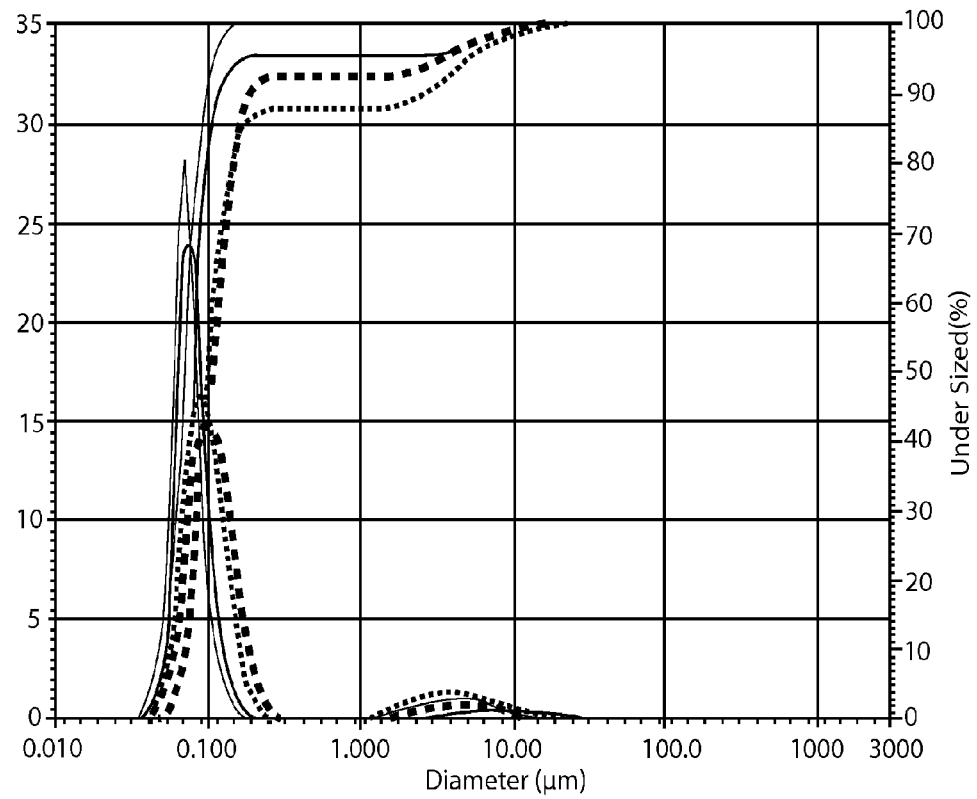
FIG. 3 shows the particle size distribution of a lipid nanoparticle formulation (Formulation 1) prepared as described in Comparative Example 1 with phosphate buffered saline (PBS) after preparation and after being vortexed for 3, 30, or 60 seconds.

The results are shown in FIGS. 1-3. As can be seen in FIG. 3, the particle size distribution of the particles prepared in PBS is bimodal. The particles are both sub- and super-1 micron in size. In contrast, the particle size distribution of the lipid particles prepared in deionized water (with and without glucose) is unimodal and does not show the presence of particles that are above 1 micron in size. See FIGS. 1 and 2.

The results for Example 2 and Comparative Example 1 are also provided in Tables 4 and 5, respectively.

TABLE 4

Lipid Nanoparticles in Deionized Water with 300 mM Glucose

| Vortex time (sec) | D10/D50/D90 (nm) |
|---|---|
| 0 | 38/48/64 |
| 30 | 44/56/75 |
| 60 | 47/58/78 |
| 120 | 59/77/107 |

TABLE 5

Lipid Nanoparticles in PBS

| Vortex time (sec) | D10/D50/D90 (nm) |
|---|---|
| 0 | 57/72/97 |
| 3 | 60/78/118 |
| 30 | 67/98/2540 |
| 60 | 71/106/189 |

Example 4

In Vivo Evaluation of Lipid Nanoparticle Formulations

The formulations prepared in Examples 1 and 2 and Comparative Example 1 were tested in mice for their anti-Factor VII activity as follows.

Figure 4:
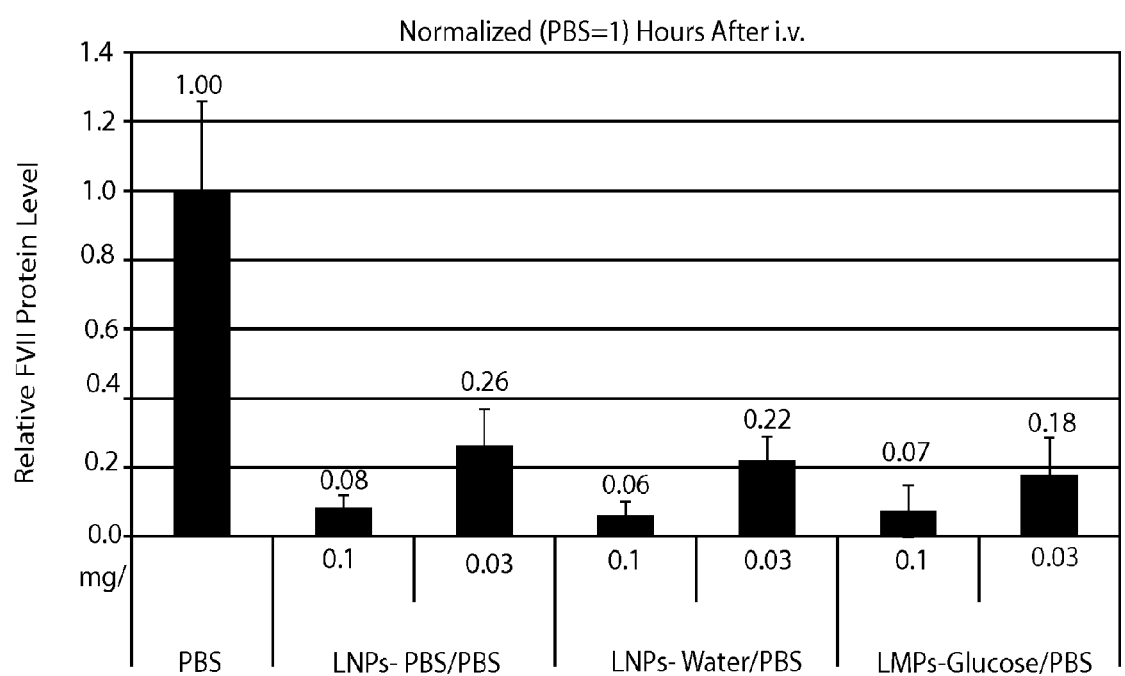
FIG. 4 shows the relative Factor VII protein level 24 hours after intravenous administration of Formulations 1-3 described in Example 2 in mice.

C57BL/6 mice (Charles River Labs, MA) received either PBS or one of the test formulations at dose of 0.1 or 0.03 mg/kg via intravenous (bolus) injection. 24 hours after administration, Factor VII levels were measured in the serum using a chromogenic assay (Coaset Factor VII, DiaPharma Group, OH or Biophen FVII, Aniara Corporation, OH) according to the manufacturer protocols. The results are shown in FIG. 4.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A pharmaceutical formulation for parenteral administration comprising
    (a) lipid nanoparticles comprising a cationic lipid and a nucleic acid, in
    (b) a medium, wherein the formulation has one or more of the following characteristics:
        (i) the medium is substantially free of anions,
        (ii) the medium is non-ionic or substantially non-ionic, and
        (iii) the formulation has a pH less than the pKa of the cationic lipid;
    and wherein the formulation further comprises an acid, and the ratio of the anion concentration from the acid to the concentration of the acid is less than about 0.5.

2. The formulation of claim 1, wherein the nucleic acid is selected from an interfering RNA, an antisense oligonucleotide, a DNAi oligonucleotide, a ribozyme, an aptamer, a plasmid, and any combination of any of the foregoing.

3. The formulation of claim 2, wherein the interfering RNA is selected from siRNA, aiRNA, miRNA, Dicer-substrate dsRNA, shRNA, ssRNAi oligonucleotides, and any combination of any of the foregoing.

4. The pharmaceutical formulation of claim 1, wherein the active pharmaceutical ingredient is a siRNA.

5. The formulation of claim 1, wherein the nucleic acid is fully encapsulated in the lipid nanoparticle.

6. The formulation of claim 1, wherein the medium comprises a non-ionic diluent.

7. The formulation of claim 6, wherein the non-ionic diluent increases the stability of the lipid nanoparticle thereby preventing aggregation.

8. The formulation of claim 1, wherein the medium comprises water.

9. The formulation of claim 8, wherein the water in the medium has been purified by reverse osmosis.

10. The formulation of claim 8, wherein the water in the medium is deionized.

11. The formulation of claim 1, wherein the medium contains less than 100 ppm of mineral acids.

12. The formulation of claim 1, wherein the lipid nanoparticles have a $d_{98}$ of less than about 150 nm.

13. The formulation of claim 1, wherein the ratio is less than about 0.3.

14. The formulation of claim 1, wherein the ratio is less than about 0.2.

15. The formulation of claim 1, wherein each nanoparticle further comprises an aggregation reducing agent.

16. The formulation of claim 15, wherein the aggregation reducing agent is a PEG-modified lipid.

17. The formulation of claim 16, wherein the PEG-lipid conjugate is a PEG-dialkyloxypropyl (PEG-DAA) conjugate or a PEG-DMG conjugate.

18. The formulation of claim 15, wherein the aggregation reducing agent is present in less than about 3 mol % in the lipid nanoparticles, based upon the total moles of lipid in the lipid nanoparticles.

19. The formulation of claim 1, wherein each nanoparticle further comprises a non-cationic lipid.

20. The formulation of claim 1, wherein the formulation comprises from about 45 to about 65% of cationic lipid, from about 5 to about 10% of a neutral lipid, from about 25 to about 40% of a sterol, and from about 0.5 to about 5% of an aggregation reducing agent, based upon 100% total moles of lipid in the lipid nanoparticles.

21. The formulation of claim 1, wherein the formulation further comprises a nonionic or substantially non-ionic isotonicity agent.

22. The formulation of claim 21, wherein the isotonicity agent is glucose.

23. The formulation of claim 1, wherein the cationic lipid has a pKa ranging from about 5 to about 7.

24. The formulation of claim 1, wherein the lipid nanoparticles have a $d_{99}$ of less than about 500 nm.

25. The formulation of claim 1, wherein the lipid nanoparticles have a $d_{99}$ of less than about 100 nm.

26. The formulation of claim 1, wherein the lipid nanoparticles contain less than 3% by weight of pegylated lipids.

27. The formulation of claim 1, wherein the lipid nanoparticles exhibit a single mode size distribution.

28. A method for decreasing, inhibiting, or preventing the aggregation of lipid nanoparticles in a pharmaceutical formulation for parenteral administration, the particles comprise a cationic lipid and a nucleic acid, the method comprising dispersing the lipid nanoparticles in a medium, where the formulation has one or more of the following characteristics:
  (i) the medium is substantially free of anions,
  (ii) the medium is non-ionic or substantially non-ionic, and
  (iii) the formulation has a pH less than the pKa of the cationic lipid:,
and wherein the formulation further comprises an acid, and the ratio of the anion concentration from the acid to the concentration of the acid is less than about 0.5.

29. A method of preparing a pharmaceutical formulation comprising:
  (i) preparing lipid nanoparticles comprising a cationic lipid and a nucleic acid in a first medium comprising a buffer; and
  (ii) changing the first medium to a second medium which is (a) non-ionic or substantially non-ionic and/or (b) free of or substantially free of anions; wherein the second medium further comprises an acid, and the ratio of the anion concentration from the acid to the concentration of the acid in the formulation is less than about 0.5.

* * * * *